United States Patent [19]
Ortiz

[11] Patent Number: 4,619,136
[45] Date of Patent: Oct. 28, 1986

[54] APPARATUS FOR MEASURING THE DECONTAMINATION FACTOR OF A MULTIPLE FILTER AIR-CLEANING SYSTEM

[75] Inventor: John P. Ortiz, Santa Fe, N. Mex.

[73] Assignee: The United States of America as represented by the United States Department of Energy, Washington, D.C.

[21] Appl. No.: 751,412

[22] Filed: Jul. 3, 1985

[51] Int. Cl.$^4$ ............................................. G01N 15/08
[52] U.S. Cl. .......................................................... 73/38
[58] Field of Search ............... 73/118, 38, 40.7, 432 R

[56] References Cited
U.S. PATENT DOCUMENTS
4,055,075 10/1977 Allan et al. ............................ 73/40.7
4,515,007 5/1985 Herman ................................... 73/38

Primary Examiner—Jerry W. Myracle
Attorney, Agent, or Firm—Lee W. Huffman; Paul D. Gaetjens; Judson R. Hightower

[57] ABSTRACT

An apparatus for measuring the overall decontamination factor of first and second filters located in a plenum. The first filter separates the plenum's upstream and intermediate chambers. The second filter separates the plenum's intermediate and downstream chambers. The apparatus comprises an aerosol generator that generates a challenge aerosol. An upstream collector collects unfiltered aerosol which is piped to first and second dilution stages and then to a laser aerosol spectrometer. An intermediate collector collects challenge aerosol that penetrates the first filter. The filtered aerosol is piped to the first dilution stage, diluted, and then piped to the laser aerosol spectrometer which detects single particles. A downstream collector collects challenge aerosol that penetrates both filters. The twice-filtered aerosol is piped to the aerosol spectrometer. A pump and several valves control the movement of aerosol within the apparatus.

11 Claims, 2 Drawing Figures

APPARATUS FOR MEASURING THE DECONTAMINATION FACTOR OF A MULTIPLE FILTER AIR-CLEANING SYSTEM

This invention is the result of a contract with the Department of Energy (Contract No. W-7405-ENG-36).

BACKGROUND OF THE INVENTION

The invention described herein relates generally to structures for measuring air-cleaning filter efficiency and more particularly to structures for measuring the decontamination factors of multiple filter air-cleaning systems.

The protection provided by an air-cleaning filter is expressed as the filter's decontamination factor. If a filter stops all but one out of one thousand incident particles, the filter's decontamination factor is $1.0 \times 10^3$. It was once thought that a two-stage filter would have an overall decontamination factor equal to the product of the decontamination factors of the individual filters. However, filtration efficiency is a function of particle size and the aerosol that penetrates the first filter may be restricted to a narrow size range from the challenge aerosol and hence be more likely to also penetrate the second filter than particles of other sizes.

Current test methods test each filter in a dual-filter system separately and may overestimate the overall decontamination factor of the dual-filter system. Moreover, these procedures for testing each filter separately require closing dampers to the process area and shutting down the process for about one hour. Temporary ducts are installed so that each filter can be tested separately. It is highly desirable to reduce the system shut-down time during testing and improve the accuracy of decontamination factor measurements.

SUMMARY OF THE INVENTION

One object of the present invention is to accurately measure the overall decontamination factor of a multiplefilter air cleaning system.

Another object of the invention is to reduce system down time when testing air-filter efficiency.

To achieve the foregoing and other objects, and in accordance with the purposes of the present invention, as embodied and broadly described herein, there is provided an apparatus for measuring the overall decontamination factor of first and second filters in a plenum having upstream, intermediate, and downstream chambers. The first filter separates the upstream and intermediate chambers and the second filter separates the intermediate and downstream chambers. The apparatus comprises an aerosol generator, in fluid communication with the upstream chamber, that generates a challenge aerosol composed of individual particles. An upstream collector in the upstream chamber collects challenge aerosol before it enters the first filter. An intermediate collector in the intermediate chamber collects challenge aerosol that passes through the first filter. A downstream collector in the downstream chamber collects challenge aerosol that passes through the second filter. A first conduit provides a path for challenge aerosol and has main, upstream, intermediate, and downstream portions. The main portion is in fluid communication with every other portion. The upstream portion is in fluid communication with the upstream collector as is the intermediate portion with the intermediate collector and as is the downstream portion with the downstream collector. An upstream valve element in the upstream portion controls the passage of challenge aerosol through the upstream collector, upstream portion and into the main portion. An intermediate valve element in the intermediate portion controls the passage of challenge aerosol through the intermediate collector, intermediate portion and into the main portion. A downstream valve element in the downstream portion controls the passage of challenge aerosol through the downstream collector, downstream portion and into the main portion. A dilution conduit with entry, middle, and exit portions provides a path for the challenge aerosol. The entry portion is in fluid communication with the main portion. A first valve element in the dilution entry portion controls the passage of challenge aerosol through the entry portion. An analysis conduit with entry, middle, laser, and exit portions provides a path for the challenge aerosol. The analysis entry portion and main portion are in fluid communication as is the analysis exit portion with the dilution exit portion. A second valve element between the analysis entry and middle portions controls the passage of challenge aerosol through the entry portion. A first dilution stage dilutes the challenge aerosol and is disposed between the dilution entry and middle portions. A transverse conduit is in fluid communication with the dilution middle portion and with the analysis middle portion. It provides a path for challenge aerosol. A third valve element in the transverse conduit controls the passage of challenge aerosol therethrough. A second dilution stage further dilutes the challenge aerosol. It is between and in fluid communication with the dilution middle and exit portions. A fourth valve element in the dilution middle portion controls the passage of challenge aerosol through the second dilution stage. A laser aerosol spectrometer detects individual particles. The laser portion provides a path for challenge aerosol between the spectrometer and the analysis middle portion. A fifth valve element in the laser portion controls the passage of challenge aerosol through the laser portion. A sixth valve element is between the analysis middle and exit portions and controls the passage of challenge aerosol between the analysis middle and exit portions. A pump is in fluid communication with the dilution exit portion and facilitates the movement of challenge aerosol within the apparatus.

One advantage of the present invention is that the overall decontamination factor of dual air filters can be measured simultaneously.

Another advantage of the invention is that time and money are saved when testing dual air filters.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION OF THE INVENTION

Figure 1:
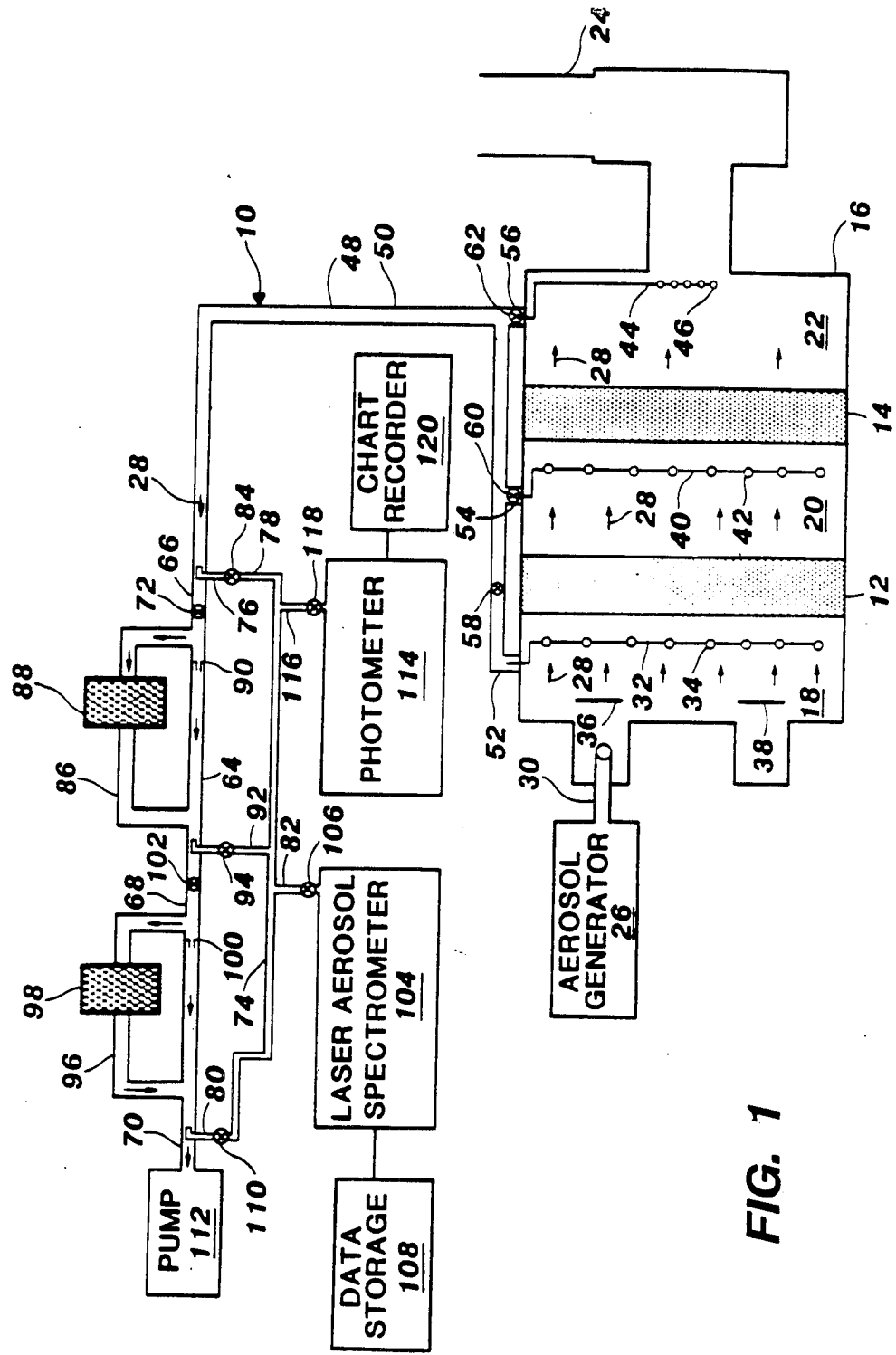
FIG. 1 shows a schematic view of an embodiment of the invention.

Reference is now made to FIG. 1 which shows a schematic view of an embodiment of the present invention. The present invention is an apparatus 10 for measuring the overall decontamination factor of a first filter 12 and a second filter 14. The filters 12, 14 to be tested are located in a plenum 16 having an upstream chamber 18, an intermediate chamber 20 and a downstream chamber 22. First filter 12 separates upstream chamber 18 from intermediate chamber 20 and second filter 14 separates intermediate chamber 20 from downstream chamber 22. Plenum 16 also includes an exhaust portion 24.

The apparatus 10 comprises an aerosol generator 26 for producing a challenge aerosol composed of individual particles. For purposes of illustration, the challenge aerosol and individual particles are represented by arrows 28, only some of which are numbered for ease of illustration and clarity. The challenge aerosol can be an aerosol of di-(2-ethylhexyl) phthalate. Aerosol generator 26 is in fluid communication, via line 30, with upstream chamber 18. It should be readily understood that the present invention is the apparatus 10 and not the plenum 16 or the filters 12, 14 to be tested, as is pointed out in the appended claims.

Apparatus 10 includes an upstream collector 32 for collecting challenge aerosol before it enters first filter 12. Upstream collector 32 is disposed in upstream chamber 18 and can include a first plurality of spaced-apart collection members 34, such as the eight shown. Apparatus 10 can include a first baffle 36 for evenly distributing the challenge aerosol within upstream chamber 18. First baffle 36 is located between aerosol generator 26 and first filter 12. A second baffle 38 can also be used.

An intermediate collector 40 for collecting challenge aerosol that passes through first filter 12 is disposed in intermediate chamber 20 and can include a second plurality of spaced-apart collection members 42, such as the eight shown. A downstream collector 44 collects challenge aerosol that passes through second filter 14. Downstream collector 44 is disposed in downstream chamber 22 and can include a third plurality of spaced-apart collection members 46, such as the five shown.

A first conduit 48 provides a path for collected challenge aerosol. First conduit 48 includes a main portion 50, and upstream portion 52, an intermediate portion 54 and a downstream portion 56. Main portion 50 is in fluid communication with upstream portion 52, intermediate portion 54 and downstream portion 56. Upstream portion 52 is in fluid communication with upstream collector 32 as is intermediate portion 54 with intermediate collector 40 and as is downstream portion 56 with downstream collector 44.

An upstream valve element 58 is disposed in upstream portion 52 and controls the passage of unfiltered challenge aerosol through upstream collector 32, through upstream portion 52 and into main portion 50. An intermediate valve element 60 is disposed in intermediate portion 54 and controls the passage of filtered challenge aerosol through intermediate collector 40, through intermediate portion 54 and into main portion 50. A downstream valve element 62 is disposed in downstream portion 56 and controls the passage of twice-filtered challenge aerosol through downstream collector 44, through downstream portion 56 and into main portion 50.

A dilution conduit 64 provides a path for challenge aerosol and has an entry portion 66, a middle portion 68 and an exit portion 70. Dilution entry portion 66 is in fluid communication with main portion 50. A first valve element 72 is disposed in dilution entry portion 66 and controls the passage of challenge aerosol through dilution entry portion 66.

An analysis conduit 74 provides a path for challenge aerosol and has an entry portion 76, a middle portion 78, an exit portion 80 and a laser portion 82. Analysis entry portion 76 is in fluid communication with main portion 50 as is analysis exit portion 80 with dilution exit portion 70. Laser portion 82 is in fluid communication with analysis middle portion 78. A second valve element 84 is disposed between analysis entry portion 76 and analysis middle portion 78 and controls the passage of challenge aerosol through analysis entry portion 76.

A first dilution stage 86 can, as shown, include a first dilution filter 88 and a first neck 90. First neck 90 restricts the flow of challenge aerosol through dilution middle portion 68. First dilution stage 86 is disposed between and in fluid communication with dilution entry portion 66 and dilution middle portion 68. First dilution stage 86 can dilute challenge aerosol by a ratio of two hundred fifty to one.

A transverse conduit 92 provides a path for challenge aerosol between, and is in fluid communication with, dilution middle portion 68 and analysis middle portion 78. A third valve element 94 is disposed in transverse conduit 92 and controls the passage of challenge aerosol therethrough.

A second dilution stage 96 can, as shown, include a second dilution filter 98 and a second neck 100. Second neck 100 has a much smaller inside diameter than dilution middle portion 68, so that it restricts the flow of challenge aerosol through dilution middle portion 68. First neck 90 has a structure similar to second neck 100. Second dilution stage 96 is disposed between and in fluid communication with dilution middle portion 68 and dilution exit portion 70. Second dilution stage 96 should dilute challenge aerosol by a ratio of at least seven hundred to one, and in the embodiment shown, dilutes it by a ratio of one thousand to one. A fourth valve element 102 is disposed in dilution middle portion 68 and controls the passage of challenge aerosol through second dilution stage 96.

A laser aerosol spectrometer 104 detects individual particles, represented by arrows 28, in the challenge aerosol. Laser aerosol spectrometer 104 is in fluid communication with laser portion 82, which provides a path for challenge aerosol between analysis middle portion 78 and laser aerosol spectrometer 104. A fifth valve element 106 is disposed in laser portion 82 and controls the passage of challenge aerosol through laser portion 82. Laser aerosol spectrometer 104 detects single particles so, to avoid counting uncertainty caused by the presence of more than one particle, only filtered or diluted challenge aerosol is routed thereto. Laser aerosol spectrometer 104 s preferably a PMS model LAS-X$^2$ from Particle Measuring Systems Inc., Boulder, Colo. This model can identify and count single particles over a size range of 0.09 to 3.0 μm diameter. Laser aerosol spectrometer 104 can be operatively connected to a data processing and storage device 108 such as a Hewlett Packard-85 microcomputer.

A sixth valve element 110 is disposed between analysis middle portion 78 and analysis exit portion 80 and controls the passage of challenge aerosol therebetween. A pump 112 is connected to and in fluid communication with dilution exit portion 70. Pump 112 facilitates the movement of challenge aerosol within apparatus 10 by varying the pressure therein and drawing challenge aerosol out of dilution exit portion 70 and out of analysis exit portion 80. Pump 112 can include a filter (not shown) for removing contaminant particles. Where plenum 16 is part of a plutonium processing facility, it is essential that pump 112 include a filter, even though apparatus 10 is used with a safe challenge aerosol to test filters 12, 14.

Apparatus 10 of the present invention can include a photometer 114 for comparing the concentration of unfiltered challenge aerosol collected by upstsream collector 32 with the concentration of unfiltered challenge aerosol that has been diluted by first dilution stage 86 or second dilution stage 96 to verify their dilution ratios. A photometer conduit 116 is in fluid communication with analysis middle portion 78 and with photometer 114 and provides a path for challenge aerosol therebetween. A seventh valve element 118 is disposed in photometer conduit 116 and controls the passage of challenge aerosol through photometer conduit 116 and into photometer 114. A chart recorder 120 can be operatively connected to photometer 114 to record dilution ratio data.

Challenge aerosol collected by upstream collector 32 is routed to first dilution stage 86 where it is diluted. It can also be routed to second dilution stage 96 to further dilute it before it is routed to laser aerosol spectrometer 104. Challenge aerosol that penetrates first filter 12 is routed to first filter stage 86, diluted, and then routed to laser aerosol spectrometer 104 for particle detection. Based on the dilution ratios of first dilution stage 86 and second dilution stage 96, and the number of particles detected in a given time period by laser aerosol spectrometer 104, decontamination factors for the overall dual filter system can be calculated, as can individual decontamination factors for first filter 12 and second filter 14.

Challenge aerosol that penetrates second filter 14 need not be diluted, but can be routed directly to spectrometer 104. Before testing the filters 12, 14 with challenge aerosol, air should be collected with downstream collector 44 and routed to spectrometer 104 to make a background particle determination.

Figure 2:
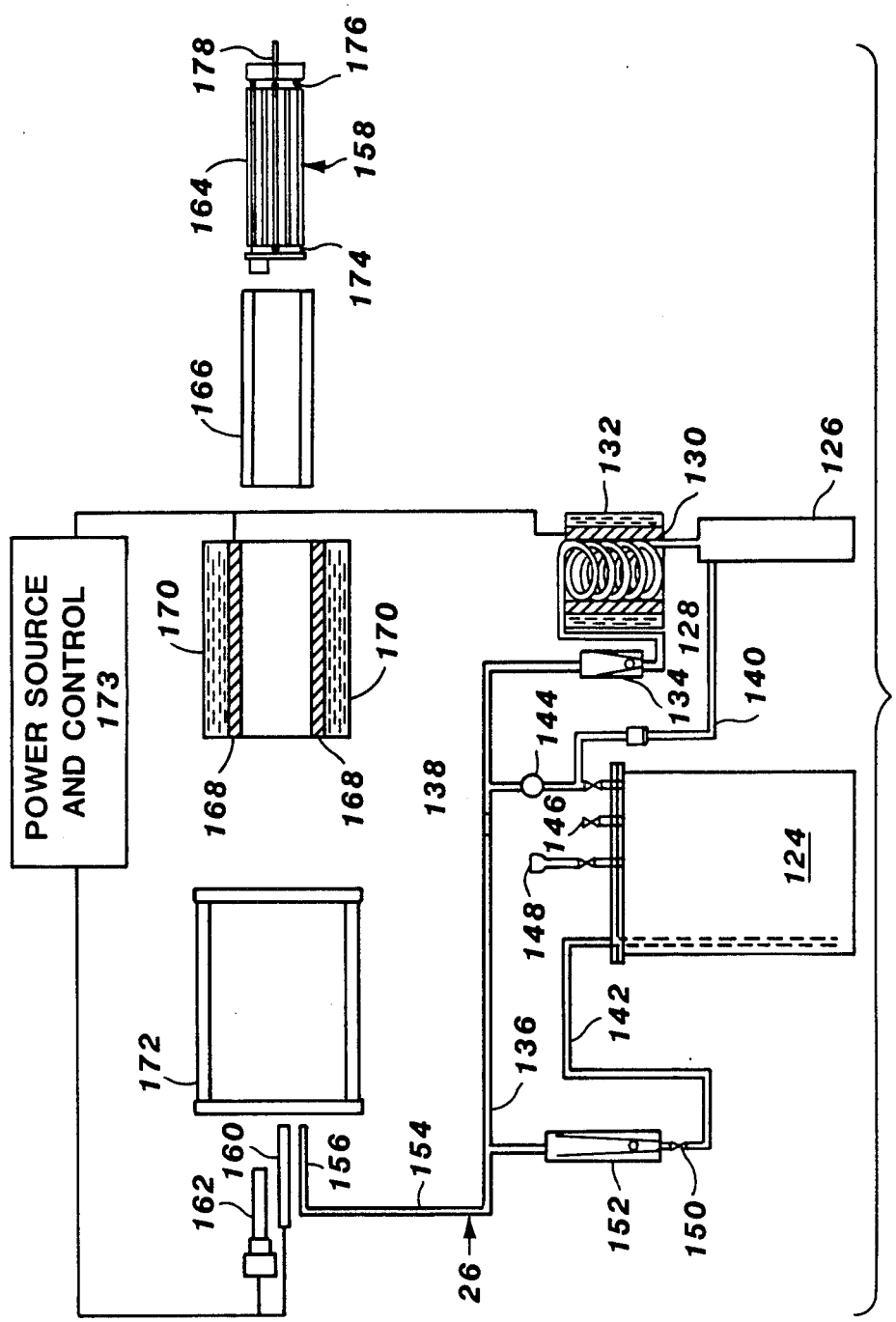
FIG. 2 shows a schematic view, partially in cross section and partially exploded, of an aerosol generator usable with the present invention.

Reference is now made to FIG. 2, which shows a schematic view, partially in crosssection and partially exploded, of a preferred embodiment of an aerosol generator 26 usable in the present invention. The aerosol generator 26 includes a reservoir 124 which holds up to ten gallons of di-(2-ethylhexyl) phthalate, hereinafter DEHP. Cylinder 126 contains $CO_2$ gas under pressure. The gas passes through coil 128 and is heated by first heater 130, which is surrounded by insulator 132. The flow rate of the gas is indicated by first flowmeter 134. The gas passes through first line 136 and first check valve 138. The gas also passes through second line 140 into reservoir 124 and forces liquid DEHP into third line 142. Reservoir 124 has a pressure gauge 144, a relief valve 146 and a DEHP filler cap 148. Liquid DEHP going through third line 142 goes through second check valve 150 and its flow rate is indicated by second flowmeter 152. Liquid DEHP and $CO_2$ gas enter fourth line 154 where they mix together. Fourth line 154 has an injection portion 156 which is received in a first tubular recess (not shown) of vapor core 158. Vapor core 158 has a second tubular recess (not shown) in which an inside heater 160 is received. Inside heater 160 is a three hundred watt heater. Vapor core 158 has a third tubular recess (not shown) in which a thermostat 162 is received. Vapor core 158 is a 76 mm diameter steel rod with twenty equally-spaced channels 164 machined on its outside surface. Vapor core 158 is contained in a core jacket 166 which is surrounded by a cylindrical eleven hundred watt outside heater 168. Insulation 170 surrounds outside heater 168. A generator housing 172, in turn, surrounds insulation 170. Outside heater 168, inside heater 160, thermostat 162, and first heater 130 are all operatively connected to a power source and control device 173. The mixture of liquid DEHP and $CO_2$ gas is routed through a slot 174 which extends from the end of injection portion 156 to the outside of vapor core 158. The liquid-gas mixture moves along channels 164, is vaporized and then routed through four passages 176 to a nozzle 178 where the vapor enters ambient temperature air, cools and condenses to form the challenge aerosol.

The foregoing description of the preferred embodiments of the invention has been presented for purposes of illustration and description. It is not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for measuring the overall decontamination factor of first and second filters, the first and second filters being located in a plenum having an upstream chamber, an intermediate chamber, and a downstream chamber, the first filter being located between the upstream and intermediate chambers and the second filter being located between the intermediate and downstream chambers, said apparatus comprising:

a. an aerosol generator for producing a challenge aerosol composed of individual particles, said aerosol generator being in fluid communication with the upstream chamber;

b. an upstream collector for collecting said challenge aerosol before said challenge aerosol enters the first filter, said upstream collector being disposed in the upstream chamber;

c. an intermediate collector for collecting said challenge aerosol that passes through the first filter, said intermediate collector being disposed in the intermediate chamber;

d. a downstream collector for collecting said challenge aerosol that passes through the second filter, said downstream collector being disposed in the downstream chamber;

e. a first conduit for providing a path for said challenge aerosol, said first conduit having a main portion, an upstream portion, an intermediate portion and a downstream portion, said main portion being in fluid communication with said upstream, intermediate, and downstream portions, said upstream portion being in fluid communication with said upstream collector, said imtermediate portion being in fluid communication with said intermediate collector and said downstream portion being in fluid communication with said downstream collector;

f. an upstream valve means for controlling the passage of said challenge aerosol through said upstream collector, through said upstream portion and into said main portion, said upstream valve means being disposed in said upstream portion;

g. an intermediate valve means for controlling the passage of said challenge aerosol through said intermediate collector, through said intermediate portion and into said main portion, said intermediate valve means being disposed in said intermediate portion;

h. a downstream valve means for controlling the passage of said challenge aerosol through said downstream collector, through said downstream portion and into said main portion, said downstream valve means being disposed in said downstream portion;

i. a dilution conduit for providing a path for said challenge aerosol, said dilution conduit having entry, middle, and exit portions, said dilution entry portion being in fluid communication with said main portion;

j. a first valve means for controlling the passage of said challenge aerosol through said dilution entry portion, said first valve means being disposed in said dilution entry portion;

k. an analysis conduit for providing a path for said challenge aerosol, said analysis conduit having entry, middle, laser, and exit portions, said analysis entry portion being in fluid communication with said main portion and said analysis exit portion being in fluid communication with said dilution exit portion;

l. a second valve means for controlling the passage of said challenge aerosol through said analysis entry portion, said second valve means being disposed between said analysis entry portion and said analysis middle portion;

m. a first dilution stage for diluting said challenge aerosol, said first dilution stage being disposed between and in fluid communication with said dilution entry portion and said dilution middle portion;

n. a transverse conduit for providing a path for said challenge aerosol between said dilution middle portion and said analysis middle portion, said transverse conduit being in fluid communication with said dilution middle portion and said analysis middle portion;

o. a third valve means for controlling the passage of said challenge aerosol through said transverse conduit, said third valve means being disposed in said transverse conduit;

p. a second dilution stage for further diluting said challenge aerosol, said second dilution stage being disposed between and in fluid communication with said dilution middle portion and said dilution exit portion;

q. a fourth valve means for controlling the passage of said challenge aerosol through said second dilution stage, said fourth valve means being disposed in said dilution middle portion;

r. a laser aerosol spectrometer for detecting said individual particles, said laser aerosol spectrometer being in fluid communication with said laser portion, said laser portion providing a path for said challenge aerosol between said analysis middle portion and said laser aerosol spectrometer, said laser portion being in fluid communication with said analysis middle portion;

s. a fifth valve means for controlling the passage of said challenge aerosol through said laser portion, said fifth valve means being disposed in said laser portion;

t. a sixth valve means for controlling the passage of said challenge aerosol between said analysis middle portion and said analysis exit portion, said sixth valve means being disposed between said analysis middle portion and said analysis exit portion; and u. a pump for facilitating the movement of said challenge aerosol within said apparatus, said pump being connected to and in fluid communication with said dilution exit portion.

2. The apparatus of claim 1 further comprising a baffle for evenly distributing said challenge aerosol within the upstream chamber, said baffle being disposed between said aerosol generator and the first filter.

3. The apparatus of claim 1 further comprising a photometer conduit for providing a path for said challenge aerosol, said photometer conduit being connected to and in fluid communication with said analysis middle portion, a photometer for comparing the concentration of said challenge aerosol with the concentration of said challenge aerosol which has been diluted to verify dilution ratios of said first and second dilution stages, said photometer being in fluid communication with said photometer conduit, and a seventh valve means disposed in said photometer conduit for controlling the passage of said challenge aerosol through said photometer conduit and into said photometer.

4. The apparatus of claim 3 further comprising a chart recorder for recording dilution ratio data, said chart recorder being operatively connected to said photometer.

5. The apparatus of claim 1 wherein said first dilution stage includes a first dilution filter for removing said challenge aerosol and thereby diluting said challenge aerosol by a ratio of about two hundred fifty to one.

6. The apparatus of claim 1 wherein said second dilution stage includes a second dilution filter for removing said challenge aerosol and thereby diluting said challenge aerosol by a ratio of at least seven hundred to one.

7. The apparatus of claim 1 wherein said challenge aerosol comprises di-(2-ethylhexyl) phthalate.

8. The apparatus of claim 1 wherein said laser aerosol spectrometer can detect said particles having a diameter from 0.09 to 3.0 $\mu$m.

9. The apparatus of claim 1 wherein said upstream collector comprises a first plurality of spaced-apart collection members.

10. The apparatus of claim 1 wherein said intermediate collector comprises a second plurality of spaced-apart collection members.

11. The apparatus of claim 1 wherein said downstream collector comprises a third plurality of spaced-apart collection members.

* * * * *